United States Patent [19]

Williams

[11] Patent Number: Plant 5,356

[45] Date of Patent: Nov. 27, 1984

[54] MINIATURE ROSE PLANT—MINACO

[76] Inventor: Ernest D. Williams, 1510 Lebanon Ave., Dallas, Tex. 75208

[21] Appl. No.: 492,018

[22] Filed: May 5, 1983

[51] Int. Cl.[3] ..... A01H 5/00

[52] U.S. Cl. ..... Plt./7

[58] Field of Search ..... Plt./7

*Primary Examiner*—Robert E. Bagwill

[57] ABSTRACT

The subject of the present disclosure is a new and distinct variety of miniature rose plant characterized by the deep lavender color of the very double flowers and by the profusion of bloom.

1 Drawing Figure

1

The present invention relates to a new and distinct variety of hardy, dwarf, bush type rose plant of the miniature class; the variety being primarily characterized—as to novelty—by the medium to deep lavender (mauve) coloration of the flowers which in general color effect are similar to Angel Face (Floribunda—U.S. Plant Pat. No. 2,792).

The variety is further characterized by:

An abundance of bloom with flowers usually borne singly.

Slight fragrance.

A plant which is vigorous, of bushy, spreading shape with semi-glossy to matt, small foliage, with pointed leaflets; the buds and flowers being similar in form and size to Over the Rainbow (miniature—U.S. Plant Pat. No. 3,472), but averaging more petals.

The plant, which has a normal height of 12 inches (30 cm) or more, can easily be maintained at lesser height by occasional trimming.

A plant which grows and blooms satisfactorily outdoors; is good for growing in pots; and provides attractive garden decoration as well as cut flowers.

The present variety of miniature rose was originated by me at my nursery located at Dallas, Tex., under conditions of careful control and observation, as a cross between Angel Face (Floribunda—U.S. Plant Pat. No. 2,792) as the seed parent and an un-named seedling (Angel Face × Over the Rainbow) as the pollen parent.

Subsequent to origination of the variety I successfully reproduced it, at my nursery located as aforesaid, by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Color Council Horticultural Color Chart, except where common terms of color definition are employed.

Type: Hardy; dwarf; bushy; spreading; seedling; outdoors; cut flowers; garden decoration; potted plant.

Class: miniature. Variety identification: Minaco. Commercial synonym; Angelglo.

Flowers borne: Usually singly on slender wirey stems.

Quantity of bloom: Abundant.

Bud:

2

*Peduncle.*—Medium length; slender but sturdy; erect; medium green, sometimes tinted bronze (outdoors); hairs — few.

*Before calyx breaks.*—Size — small. Form short; pointed with few foliaceous appendages and few or no tiny hairs on surface of bud; with foliaceous parts extending beyond the tip of the bud equal to one-half or less of its length. Color — medium green, occasionally tinted with bronze (outdoors).

*As calyx breaks.*—Color — deep reddish, sometimes becoming greenish white near base.

*Opening.*—Opens well in all weather.

Bloom:

*Size when fully open.*—Small averaging about 35–40 mm (1½"). Petalage very double — averaging about 35–40 petals, arranged regularly plus sometimes several small petaloids.

*form.*—High centered, with petals reflexing loosely outward, and later at maturity, rolled loosely outward and downward. Open flowers usually show no stamens.

Petals: Fairly thick; satiny on inside and on outside surface.

*Shape.*—Outside petals, broad lanceolate — almost round; intermediate — broad lanceolate with rounded tip; inside — lanceolate with rounded tip.

Color: Newly opened flower from a plant grown outdoors (1982 season), Dallas, Tex.:

*Outside petal.*—Outside surface — near (or similar to) Lilac Purple 031/1 shading into a color near Magnolia Purple 030 on basal ½ of petal, with spot of near white at base. Inside surface — near Lilac Purple 031/1 or 031/2 becoming darker near base with small yellowish area at base.

*Intermediate petal.*—Outside surface — similar to outside petal. Inside surface similar to outside petal.

*Inner petal.*—Outside surface — same as intermediate petal; inside surface — same as intermediate petal. Note: the above coloration maybe (and often is) modified by reddish veining or reddish undertone and/or overlaid with a grayish coloration. In general the color is similar to Angel Face but darker. Mature flowers often have a grayed effect as they age.

*General color effect.*—Newly opened flowers — medium to deep lavender or lilac color. Three days open — color similar to newly opened flowers but less brilliant.

*Behavior.*—Opens well in all weather.

*Flower longevity* (*May* 1982).—Plant in pot 6–8 days or longer. Cut flowers at living room temperature 4–5 days or longer.

Reproductive Organs:

*Stamens.*—Few or none.

*Filaments.*—Few or none.

*Anthers.*—Few or none.

*Pollen.*—None.

*Pistils.*—Average number.

*Styles.*—Fairly even; short length; bunched.

*Ovaries.*—All enclosed in calyx.

*Hips.*—None.

*Sepals.*—Permanent; spear shaped, recurved against peduncle.

*Seed.*—None.

Foliage:

*Leaves.*—Compound of five (sometimes three) leaflets; fairly small; leathery; semi-glossy to matt.

*Leaflets.*—Shape: broad, nearly oval, apex acute; base rounded or rounded acute. Margin serrate. Color: medium to dark green; new growth — normal (medium) green (sometimes lightly tinted reddish). Rachis: medium strength; upper side — usually few or no prickles or hairs, grooved; under side sparsely thorny with few or no tiny prickles. Stipules: medium long; narrow to medium width; medium length; narrow points which turn out usually at about 45 degrees.

Growth:

*Habit.*—Dwarf; bushy; upright to spreading; much branched.

*Growth.*—Vigorous; internodes short.

*Canes.*—Medium; slender; sturdy.

*Main stems.*—Color: medium green.

*Thorns.*—Few; slender, nearly straight, inclined slightly downward; color — brown. Prickles — none. Hairs — none.

*Branches.*—Color: medium green. Thorns — average to few; medium length; slender; nearly straight; inclined downward. Medium oval base. Prickles: none. Hairs: none.

The miniature rose plant and its flowers as herein described may vary in slight detail due to climatic, soil and cultural conditions under which the variety may be grown; the present description being of the variety as grown at Dallas, Tex.

The following is claimed:

1. A new and distinct variety of miniature rose plant of hardy, dwarf, bushy, much branched habit, substantially as illustrated and described, characterized by buds and flowers of a mauve or lavender color, being of a shade generally near Lilac Purple 031/1 to 031/2, the bud and flower resembling the variety Over the Rainbow (U.S. Plant Pat. No. 3,472) in form and size but having more petals; and further characterized by a plant of vigorous and compact growth habit, easy to propagate from cuttings, with an abundance of flowers borne usually one to the stem.

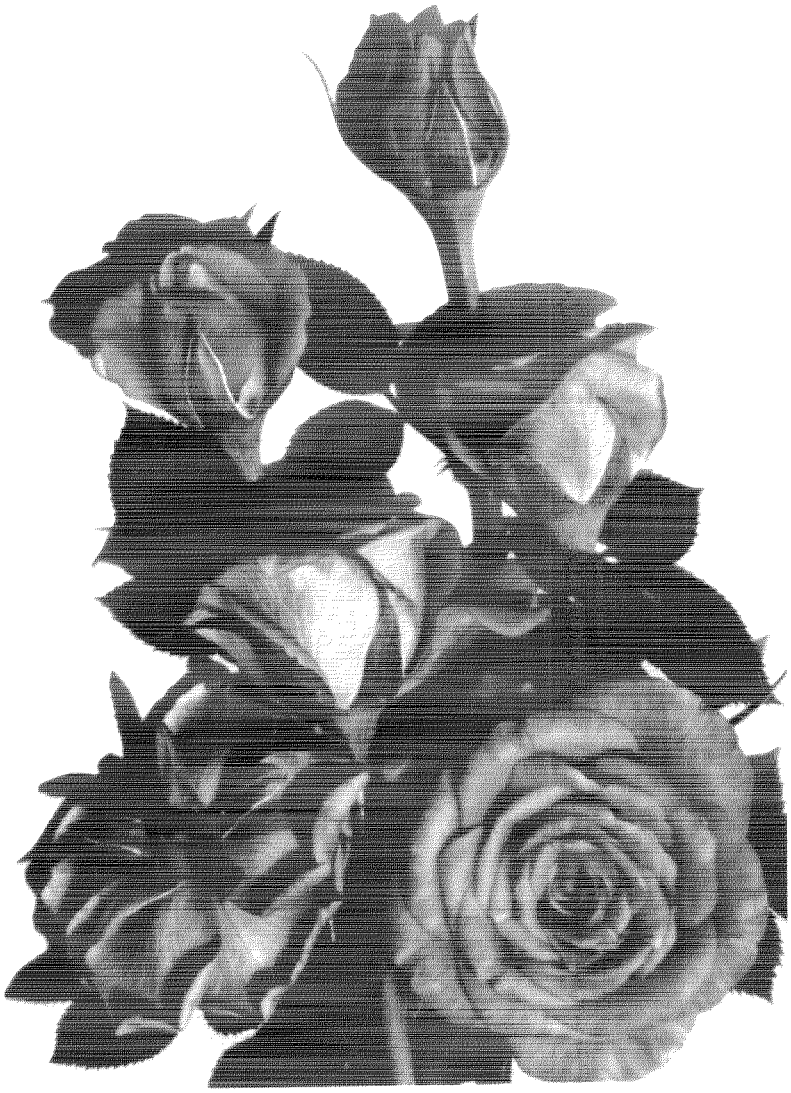

* * * * *